US010850247B2

(12) United States Patent
Walters et al.

(10) Patent No.: US 10,850,247 B2
(45) Date of Patent: Dec. 1, 2020

(54) PROCESS WITH PHOTOPOLYMERIZATION FOR PREPARING MICROCAPSULES OF CONTROLLED SIZE

(71) Applicant: CALYXIA, Bonneuil-sur-Marne (FR)

(72) Inventors: Jamie Walters, Paris (FR); Damien Demoulin, Paris (FR)

(73) Assignee: CALYXIA, Bonneuil-sur-Marne (FR)

( * ) Notice: Subject to any disclaimer, the term of this patent is extended or adjusted under 35 U.S.C. 154(b) by 0 days.

(21) Appl. No.: 16/698,218

(22) Filed: Nov. 27, 2019

(65) Prior Publication Data

US 2020/0094214 A1 Mar. 26, 2020

Related U.S. Application Data

(63) Continuation of application No. 16/466,001, filed as application No. PCT/EP2017/081227 on Dec. 1, 2017.

(51) Int. Cl.

| | |
|---|---|
| ***B01J 13/16*** | (2006.01) |
| ***C08F 2/48*** | (2006.01) |
| ***C08F 2/22*** | (2006.01) |
| ***C08L 57/00*** | (2006.01) |
| ***C08L 87/00*** | (2006.01) |

(52) U.S. Cl.

CPC ................ *B01J 13/16* (2013.01); *C08F 2/22* (2013.01); *C08F 2/48* (2013.01); *C08L 57/00* (2013.01); *C08L 87/00* (2013.01); *C08F 2500/17* (2013.01); *C08L 2312/00* (2013.01)

(58) Field of Classification Search

CPC ... B01J 13/16; B01J 13/14; C08F 2/22; C08F 2/48; C08F 2500/17; C08F 2/50; C08F 222/10; C08F 290/067; C08L 87/00; C08L 57/00; C08L 2312/00; C08L 87/00; A61K 9/5026; A61K 8/87; A61K 9/5089; A61K 8/84; A61K 2800/412; A61K 2800/10; A61K 8/11; A61Q 19/00; A01N 25/28; C11D 17/0039; F28D 20/023

See application file for complete search history.

(56) References Cited

U.S. PATENT DOCUMENTS

2002/0160109 A1* 10/2002 Yeo .......................... A61P 5/00 427/213.3
2008/0233201 A1* 9/2008 Royere .................... B01J 13/04 514/1.1
2018/0185809 A1* 7/2018 Walters ................. A61Q 19/00

FOREIGN PATENT DOCUMENTS

WO WO-2017046360 A1 * 3/2017 ............ A01N 25/28

* cited by examiner

*Primary Examiner* — Irina S Zemel

(74) *Attorney, Agent, or Firm* — Knobbe, Martens, Olson & Bear, LLP

(57) ABSTRACT

Solid microcapsules are prepared by adding, with stirring, a composition having at least one active ingredient to a photocrosslinkable polymeric composition to obtain an emulsion, and adding the emulsion, with stirring, to a viscous composition. The viscosity of the viscous composition is greater than 2000 mPa·s at 25° C. A double emulsion is obtained, to which shear is applied at a rate less than 1000 $s^{-1}$, to obtain a sheared emulsion. Polymerization of the sheared emulsion is accomplished by photopolymerization.

12 Claims, No Drawings

PROCESS WITH PHOTOPOLYMERIZATION FOR PREPARING MICROCAPSULES OF CONTROLLED SIZE

PRIORITY AND CROSS REFERENCE TO RELATED APPLICATIONS

This application is a Continuation Application of U.S. application Ser. No. 16/466,001, filed May 31, 2019, which is the U.S. National Phase Application under 35 U.S.C. § 371 of International Application No. PCT/EP2017/081227, filed Dec. 1, 2017, designating the U.S. and published as WO 2018/100179 A1 on Jun. 7, 2018, which claims the benefit of French Application No. FR 16 61787, filed Dec. 1, 2016. Any and all applications for which a foreign or a domestic priority is claimed is/are identified in the Application Data Sheet filed herewith and is/are hereby incorporated by reference in their entireties under 37 C.F.R. § 1.57.

FIELD

The present disclosure relates to a process for preparing microcapsules.

SUMMARY

The present disclosure relates to a method for preparing microcapsules of controlled-size comprising a photopolymerization step.

DETAILED DESCRIPTION

The present invention relates to a method for preparing microcapsules of controlled-size comprising a photopolymerization step.

In many industries, in particular the chemical, cosmetic, agrochemical, paint or fuel and lubricant industries, it is important to encapsulate and isolate an active ingredient from the surrounding environment in order to protect the active ingredient against hydrolysis, thermal degradation, oxidation or other processes that may reduce the performance of the active ingredient. In addition, many applications within these industries require that the capsules produced have a narrow size range typically in the micrometer range (especially between 0.1 μm and 20 μm) in order, for example, to have better control over their overall performance.

The issue of isolating an active ingredient from the surrounding environment to improve active ingredient performance is a relatively new area for a number of industries. In most non-organic industries, performance losses associated with factors such as hydrolysis, thermal degradation, oxidation, and cross-reactivity are resolved by increasing the concentration of the active ingredient in order to achieve the desired level of performance, but which increases the cost and also generates other problems associated with the product formed in such processes.

In recent years, a large number of encapsulation methods have been developed and reported in the literature, including spray drying, solvent evaporation, interfacial polymerization and centrifugal extrusion among many others. However, for encapsulation methods on an industrial scale, emulsion techniques dominate. Such methods use a step of forming an emulsion of a hydrophobic oil or a waxy phase, dispersed in an aqueous medium or, alternatively, an aqueous phase, dispersed in a hydrophobic oil or a waxy medium. The two phases are emulsified using either a homogenizer or a stirred vessel equipped with baffles, and then stabilized using surfactants, lipids or polymeric emulsifiers. Alternatively, a reaction at the interface between the two phases may be used for the formation of a polymer envelope.

However, these systems produce emulsions and capsules that are polydisperse or are too large (above 20 μm).

In addition, these systems require the use of water to form one of the phases. They also require the use of surfactants or similar emulsifiers to stabilize the emulsion, but these have the disadvantage of being able to react with the encapsulant or providing contaminants in the different phases.

The present invention aims to provide capsules containing an active ingredient by implementing a bulk method to meet the volumes required to meet the demands of non-biologic industries.

The present invention also aims to provide a encapsulation method with double emulsion for obtaining controlled-size capsules, in particular smaller than 20 μm, or even 5 μm.

The present invention also aims to provide an encapsulation method of actives that may be implemented in the absence of water and/or surfactants and emulsifiers.

Thus, the present invention relates to a method for preparing solid microcapsules comprising the following steps:

a) the addition, with stirring, of a composition C1, comprising at least one active ingredient, in a photocrosslinkable polymer composition C2 the compositions C1 and C2 not being miscible with each other, wherein an emulsion (E1) comprising drops of composition C1 dispersed in composition C2, is obtained;

b) the addition, with stirring, of the emulsion (E1) in a composition C3, the compositions C2 and C3 not being miscible with each other, the viscosity of the composition C3 being greater than the viscosity of the emulsion (E1), and being greater than 2,000 mPa·s at 25° C., wherein a double emulsion (E2) comprising drops dispersed in the composition C3, is obtained;

c) applying shear to the emulsion (E2), the applied shear rate being less than 1000 $s^{-1}$, wherein a double emulsion (E3) is obtained comprising controlled-size drops dispersed in the composition C3; and d) the photopolymerization of the composition C2, wherein solid microcapsules dispersed in the composition C3 are obtained.

The method of the invention thus allows the production on an industrial scale of populations of double emulsion drops of controlled-size and, in particular, less than 20 μm. The control of the size of the capsules obtained by the method of the invention is due, in particular, to the control of the viscoelasticity of the compositions C2 and C3.

The method of the invention allows the production of size-controlled capsules by the implementation of a photopolymerization step, in particular UV crosslinking, of the intermediate phase of the double emulsion. This photopolymerization step makes it possible, in particular, to solidify the intermediate layer of the capsules and thus eliminates any coalescence.

Preferably, the microcapsules obtained according to the method of the invention have a mean diameter (as measured by optical microscopy or by TEM or by light diffusion technique) of between 0.1 μm and 20 μm, and preferably between 1 μm and 20 μm.

Step a)

During step a), a composition C1 is added to a photocrosslinkable polymeric composition C2, this step being carried out with stirring, which means that the composition C2 is stirred, typically mechanically, while the composition C1 is added, in order to emulsify the mixture of compositions C1 and C2.

The addition of the composition C1 in the composition C2 is typically carried out dropwise.

During step a), the composition C1 is at a temperature of between 0° C. and 100° C., preferably between 10° C. and 80° C., and preferably between 15° C. and 60° C. During step a), the composition C2 is at a temperature of between 0° C. and 100° C., preferably between 10° C. and 80° C., and preferably between 15° C. and 60° C.

Under the conditions of addition of step a), the compositions C1 and C2 are not miscible with each other, which means that the amount (by weight) of the composition C1 capable of being solubilized in the composition C2 is less than or equal to 5%, preferably less than 1%, and preferably less than 0.5%, relative to the total weight of composition C2, and that the amount (by weight) of the composition C2 capable of being solubilized in composition C1 is less than or equal to 5%, preferably less than 1%, and preferably less than 0.5%, relative to the total weight of composition C1.

Thus, when the composition C1 comes into contact with the composition C2 with stirring, the latter is dispersed in the form of drops, called simple drops.

The immiscibility between compositions C1 and C2 also makes it possible to avoid the migration of the active ingredient from composition C1 to composition C2.

Composition C2 is stirred to form an emulsion comprising drops of composition C1 dispersed in composition C2. This emulsion is also called "simple emulsion" or C1-in-C2 emulsion.

To implement step a), any type of stirrer usually used to form emulsions, such as, for example, a mechanical stirrer, a static emulsifier, an ultrasonic homogenizer, a membrane homogenizer or a high pressure homogenizer, a colloid mill, a high shear disperser or a high speed homogenizer, may be used.

Composition C1

The composition C1 comprises at least one active ingredient A. In the method of the invention, this composition C1 serves as a carrier for the active ingredient A within the drops formed during the method of the invention, and the solid capsules so obtained.

According to a first variant of the method of the invention, the composition C1 is monophasic, i.e. it is the pure active ingredient A or a solution comprising the active ingredient A in solubilized form.

According to one embodiment, the active ingredient is solubilized in composition C1.

According to this variant, the composition C1 typically consists of a solution of the active ingredient A in an aqueous solution, or an organic solvent, or a mixture of organic solvents, the active ingredient A being present in a mass content of between 1% and 99%, relative to the total mass of the composition C1. The active ingredient A may be present in a mass content ranging from 5% to 95%, from 10% to 90%, from 20% to 80%, from 30% to 70%, or from 40% to 60%, relative to the total mass of the composition C1.

According to one embodiment, the composition C1 consists of the active ingredient A.

According to another embodiment of the invention, the composition C1 is a biphasic composition, which means that the active ingredient is dispersed, either in liquid form or in solid form, in the composition C1 and is not totally solubilized in the composition C1.

According to one embodiment, the active ingredient is dispersed in the form of solid particles in the composition C1.

According to this embodiment, the composition C1 may consist of a dispersion of solid particles of the active ingredient in an organic solvent or in a mixture of organic solvents.

According to this embodiment, the composition C1 may consist of a dispersion of solid particles of the active ingredient in an aqueous phase, which comprises water and optionally hydrophilic organic solvents.

The active ingredient used is for example:

- a crosslinking agent, a hardener, an organic or metal catalyst (such as an organometallic or inorganometallic complex of platinum, palladium, titanium, molybdenum, copper, zinc) used to polymerize polymer and elastomer formulations; rubber, paint, adhesive, seal, mortar, varnish or coating;
- a dye or a pigment for formulations of elastomers, paint, coating, adhesive, seal, mortar, or paper;
- a fragrance (as defined by the International Fragrance Association (IFRA) molecule list, and available on the www.ifraorg.org website) for detergents such as detergent products, home care products, cosmetic and personal care products, textiles, paints, coatings;
- an aroma, a vitamin, an amino acid, a protein, a lipid, a probiotic, an antioxidant, a pH corrector, a preservative for food compounds and animal feed;
- a softener, a conditioner for detergents, detergent products, cosmetics and personal care products. As such, the usable active ingredients are, for example, listed in U.S. Pat. Nos. 6,335,315 and 5,877,145;
- an anti-discoloration agent (such as an ammonium derivative), an antifoam agent (such as an alcohol ethoxylate, an alkylbenzene sulfonate, a polyethylene ethoxylate, an alkylethoxysulphate or alkylsulphate) for detergents, detergent products and home care products;
- a brightening agent, also called a color activator (such as a stilbene derivative, a coumarin derivative, a pyrazoline derivative, a benzoxazole derivative or a naphthalimide derivative) intended for detergents, detergent products, cosmetics and personal care products;
- a biologically-active compound such as an enzyme, a vitamin, a protein, a plant extract, an emollient agent, a disinfecting agent, an antibacterial agent, an anti-UV agent, a drug intended for cosmetic and skincare products, to textiles. Among these biologically-active compounds are included: vitamins A, B, C, D and E, para-aminobenzoic acid, alpha hydroxy acids (such as glycolic acid, lactic acid, malic acid, tartaric acid or citric acid), camphor, ceramides, polyphenols (such as flavonoids, phenolic acid, ellagic acid, tocopherol, ubiquinol), hydroquinone, hyaluronic acid, isopropyl isostearate, isopropyl palmitate, oxybenzone, panthenol, proline, retinol, retinyl palmitate, salicylic acid, sorbic acid, sorbitol, triclosan, tyrosine;
- a disinfecting agent, an antibacterial agent, an anti-UV agent, for paints and coatings;
- a fertilizer, herbicide, insecticide, pesticide, fungicide, repellent or disinfectant for agrochemicals;
- a fire-proofing agent, also called a flame retardant, (such as a brominated polyol such as tetrabromobisphenol A, a halogenated or non-halogenated organophosphorus compound, a chlorinated compound, an aluminum trihydrate, an antimony oxide, a zinc borate, red phosphorus, melamine, or magnesium dihydroxide) for use in plastics, coatings, paints and textiles;

- a photonic crystal or photochromophore for paints, coatings and polymeric materials forming curved and flexible screens;
- a product known to those skilled in the art as phase change materials (PCM) capable of absorbing or returning heat when they undergo a phase change, intended for the storage of energy. Examples of PCM and their applications are described in Farid et al., Energy Conversion and Management, 2004, 45 (9-10), 1597-1615. As examples of PCM, mention may be made of molten salts of aluminum phosphate, ammonium carbonate, ammonium chloride, cesium carbonate, cesium sulfate, calcium citrate, calcium chloride, calcium hydroxide, calcium oxide, calcium phosphate, calcium saccharate, calcium sulfate, cerium phosphate, iron phosphate, lithium carbonate, lithium sulfate, magnesium chloride, magnesium sulphate, manganese chloride, manganese nitrate, manganese sulphate, potassium acetate, potassium carbonate, potassium chloride, potassium phosphate, rubidium carbonate, rubidium sulphate, disodium tetraborate, sodium acetate, sodium bicarbonate, sodium bisulfate, sodium citrate, sodium chloride, sodium hydroxide, sodium nitrate, sodium percarbonate, sodium persulfate, sodium phosphate, sodium propionate, sodium selenite, sodium silicate, sodium sulfate, sodium tellurate, sodium thiosulfate, strontium hydrophosphate, zinc acetate, zinc chloride, sodium thiosulfate, hydrocarbon paraffinic waxes, polyethylene glycols.

Composition C2

The composition C2 is a photocurable composition which means that it is a composition capable of polymerizing (crosslinking) to give a solid material, to form the polymerized envelope of the solid microcapsules of the invention.

According to one embodiment, the composition C2 is a liquid whose viscosity at 25° C. is between 500 mPa·s and 100,000 mPa·s.

The viscosity is measured by means of a Haake Rheostress™ 600 rheometer equipped with a cone of diameter 60 mm and angle 2 degrees, and a temperature control cell set at 25° C. The value of the viscosity is read for a shear rate of 10 $s^{-1}$.

Preferably, the viscosity of the composition C2 at 25° C. is between 1000 mPa·s and 50,000 mPa·s, preferably between 2000 mPa·s and 25,000 mPa·s, and, for example, between 3000 mPa·s and 15,000 mPa·s.

Preferably, the viscosity of the composition C2 is greater than the viscosity of the composition C1.

According to this embodiment, regardless of the viscosity of the active ingredient or its chemical properties, the destabilization kinetics of the drops of the emulsion (E1) is significantly slow, which allows the envelope of the microcapsules to be polymerized during step d) before the emulsion is destabilized. The polymerization, once completed, then provides a thermodynamic stabilization.

Thus, the relatively high viscosity of the composition C2 ensures the stability of the emulsion (E1) obtained at the end of step a).

Preferably, the interfacial tension between compositions C1 and C2 is low. Typically, these interfacial tensions vary between 0 mN/m and 50 mN/m, preferably between 0 mN/m and 20 mN/m.

The low interfacial tension between the compositions C1 and C2 also advantageously makes it possible to ensure the stability of the emulsion (E1) obtained at the end of step a).

According to one embodiment, the ratio between the volume of composition C1 and the volume of composition C2 varies between 1:10 and 10:1. Preferably, this ratio is between 1:3 and 5:1, preferably between 1:3 and 3:1.

This ratio may be adapted to control the thickness of the envelope of the polymerized microcapsules.

According to one embodiment, the composition C2 comprises at least one monomer or polymer, at least one crosslinking agent and at least one photoinitiator.

According to one embodiment, the composition C2 comprises from 50% to 99% by weight of monomer or polymer, or a mixture of monomers or polymers, relative to the total weight of the composition C2.

According to one embodiment, the composition C2 comprises from 1% to 20% by weight of crosslinking agent or of a mixture of crosslinking agents, relative to the total weight of the composition C2.

According to one embodiment, the composition C2 comprises from 0.1% to 5% by weight of photoinitiator or a mixture of photoinitiators, relative to the total weight of the composition C2.

According to one embodiment, the composition C2 comprises from 0.001% to 70% by weight of crosslinking agent with respect to the weight of the composition C2.

According to the invention, the term "monomer" or "polymer" denotes any base unit suitable for the formation of a solid material by polymerization, either alone or in combination with other monomers or polymers.

These monomers may be chosen from monomers comprising at least one reactive functional group chosen from the group consisting of acrylate, methacrylate, vinyl ether, N-vinyl ether, mercaptoester, thiolene, siloxane, epoxy, oxetane, urethane, isocyanate and peroxide functions.

In particular, the monomers may be chosen from monomers bearing at least one of the aforementioned reactive functional groups and additionally bearing at least one functional group selected from the group consisting of primary, secondary and tertiary alkylamine functions, quaternary amine functional groups, functions of sulfate, sulfonate, phoshate, phosphonate, carboxylate, hydroxyl, halogen, and mixtures thereof.

The polymers used in the composition C2 may be chosen from polyethers, polyesters, polyurethanes, polyureas, polyethylene glycols, polypropylene glycols, polyamides, polyacetals, polyimides, polyolefins, polysulphides and polydimethylsiloxanes, the polymers additionally bearing at least one reactive function chosen in the group consisting of acrylate, methacrylate, vinyl ether, N-vinyl ether, mercaptoester, thiolene, siloxane, epoxy, oxetane, urethane, isocyanate and peroxide functions.

Examples of such polymers include, but are not limited to, the following polymers: poly(2-(1-naphthyloxy)-ethyl acrylate), poly(2-(2-naphthyloxy)-ethyl acrylate), poly(2-(2-naphthyloxy)-ethyl methacrylate), polysorbitol dimethacrylate, polyacrylamide, poly((2-(1-naphthyloxy) ethanol), poly(2-(2-naphthyloxy) ethanol), poly(1-chloro-2),3-epoxypropane), poly(n-butyl isocyanate), poly(N-vinyl carbazole), poly(N-vinyl pyrrolidone), poly(p-benzamide), poly (p-chlorostyrene), poly(p-methyl styrene) poly(p-phenylene oxide), poly(p-phenylene sulfide), poly(N-(methacryloxyethyl)-succinimide), polybenzimidazole, polybutadiene, polybutylene terephthalate, polychloral, polychlorinated trifluoroethylene, polyether imide, polyether ketone, polyether sulfone, polyhydridosilsesquioxane, poly(m-phenylene isophthalamide), poly(methyl-2-acrylamido-2-methoxyacetate), poly(2-acrylamido-2-methylpropanesulfonic acid), poly-mono-butyl maleate, polybutyl methacrylate, poly(N-tert-butylmethacrylamide), poly(N-butyl methacrylamide), polycyclohexylmethacrylamide, poly(m-xylenebisacrylamide 2,3-dimethyl-1,3-butadiene, N,N-dimethylmethacrylamide), poly(n-butyl methacrylate), poly(cyclohexyl methacrylate), polyisobutyl methacrylate, poly(4-cyclohexylstyrene), polycyclol acrylate, polycyclol methacrylate, polydiethyl ethoxymethylenemalonate, poly(2,2,2-trifluoroethyl methacrylate), poly(1,1,1-trimethylolpropane trimethacrylate) polymethacrylate, poly(N, N-dimethylaniline, dihydrazide), poly(isophthalic dihydrazine), isophthalic polyacid, polydimethyl benzilketal, epichlorohydrin, poly(ethyl-3,3-diethoxyacrylate), poly(ethyl-3,3-dimethylacrylate), poly (ethyl vinyl ketone), poly(vinyl ethyl ketone), poly(penten-3-one), polyformaldehyde poly(diallyl acetal), polyfumaronitrile, polyglyceryl propoxy triacrylate, polyglyceryl trimethacrylate, polyglycidoxypropyltrimethoxysilane, polyglycidyl acrylate, poly(n-heptyl acrylate), poly(n-heptyl acrylic acid ester), poly(n-heptyl methacrylate), poly(3-hydroxypropionitrile), poly(2-hydroxypropyl acrylate), poly(2-hydroxypropyl methacrylate) poly(N-(methacryloxyethyl)-phthalimide), poly(1,9-nonanediol diacrylate), poly(1,9-nonanediol dimethacrylate), poly(N-(n-propyl) acrylamide), poly(orthophthalic acid), poly(iso-phthalic acid), poly(1,4-benzenedicarboxylic acid), poly(1,3-benzenedicarboxylic acid), poly (phthalic acid), poly(mono-2-acryloxyethyl ester), terephthalic polyacid, phthalic polyanhydride polyethylene glycol diacrylate, polyethylene glycol methacrylate, polyethylene glycol dimethacrylate, polyisopropyl acrylate, polysorbitol pentaacrylate, polyvinyl bromoacetate, polychloroprene, poly(di-n-hexylsilylene), poly(di-n-propylsiloxane), polydimethylsilylene, polydiphenyl siloxane, polyvinyl propionate, polyvinyl triacetoxysilane, polyvinyl tris-tert-butoxysilane, polyvinyl butyral, polyvinyl alcohol, polyvinyl acetate, polyethylene co-vinyl acetate, poly(bisphenol-A-polysulfone), poly(1,3-dioxepane), poly(1,3-dioxolane), poly(1,4-phenylene vinylene), poly(2,6-dimethyl-1A-phenylene oxide), poly(4-hydroxybenzoic acid), poly(4-methyl pentene-1), poly(4-vinylpyridine), polymethylacrylonitrile, polymethylphenylsiloxane, polymethylsilmethylene, polymethylsilsesquioxane, poly(phenylsilsesquioxane), poly(pyromellitimide-1,4-diphenyl ether), polytetrahydrofuran, polythiophene, poly(trimethylene oxide), polyacrylonitrile, polyether sulfone, polyethylene-co-vinyl acetate, poly(perfluoroethylene propylene), poly (perfluoroalkoxyl alkane), or poly(styrene-acrylonitrile).

"Crosslinking agent" is understood to mean a compound carrying at least two reactive functional groups capable of crosslinking a monomer or a polymer, or a mixture of monomers or polymers, during its polymerization.

The crosslinking agent may be chosen from molecules bearing at least two functional groups selected from the group consisting of acrylate, methacrylate, vinyl ether, N-vinyl ether, mercaptoester, thiolene, siloxane, epoxy, oxetane, urethane, isocyanate and peroxide functions.

As a crosslinking agent, may be mentioned, in particular:

- diacrylates, such as 1,6-hexanediol diacrylate, 1,6-hexanediol dimethacrylate, polyethylene glycol dimethacrylate, 1,9-nonanediol dimethacrylate, 1,4-butanediol dimethacrylate, 2,2-bis(4)-methacryloxyphenyl) propane, 1,3-butanediol dimethacrylate, 1,10-decanediol dimethacrylate, bis(2-methacryloxyethyl) N,N'-1, 9-nonylene biscarbamate, 1,4-butanediol diacrylate, ethylene glycol diacrylate 1,5-pentanediol dimethacrylate, 1,4-phenylene diacrylate, allyl methacrylate, N,N'-methylenebisacrylamide, 2,2-bis[4-(2-hydroxy-3-methacryloxypropoxy) phenyl] propane, tetraethylene glycol diacrylate, ethylene glycol dimethacrylate, diethylene glycol diacrylate, triethylene glycol diacrylate, triethylene glycol dimethacrylate, polyethylene glycol diglycidyl ether, N,N-diallylacrylamide, 2,2-bis [4-(2-acryloxyethoxy) phenyl] propane, glycidyl methacrylate;
- multifunctional acrylates such as dipentaerythritol pentaacrylate, 1,1,1-trimethylolpropane triacrylate, 1,1,1-trimethylolpropane trimethacrylate, ethylenediamine tetramethacrylate, pentaerythritol triacrylate, pentaerythritol tetraacrylate;
- crylates which also have another reactive function, such as propargyl methacrylate, 2-cyanoethyl acrylate, tricyclodecane dimethanol diacrylate, hydroxypropyl methacrylate, N-acryloxysuccinimide, N-(2-hydroxypropyl) methacrylamide, N-(3-aminopropyl) methacrylamide hydrochloride, N-(t-BOC-aminopropyl) methacrylamide, 2-aminoethyl methacrylate hydrochloride, monoacryloxyethyl phosphate, o-nitrobenzyl methacrylate, acrylic anhydride, 2-(tert-butylamino) ethyl methacrylate, N,N-diallylacrylamide, glycidyl methacrylate, 2-hydroxyethyl acrylate, 4-(2-acryloxyaheoxy)-2-hydroxybenzophenone, N-(phthalimidomethyl) acrylamide, cinnamyl methacrylate.

By "photoinitiator" is meant a compound capable of fragmenting under the effect of light radiation.

The photoinitiators which may be used according to the present invention are known to those skilled in the art and are described, for example in "Les photoinitiateurs dans la réticulation des revêtements", G. Li Bassi, Double Liaison—Chimie des Peintures, No. 361, November 1985, p. 34-41; "Applications industrielles de la polymérisation photoinduite", Henri Strub, L'Actualité Chimique, February 2000, p. 5-13; and "Photopolymères: considérations théoriques et réaction de prise", Marc, J. M. Abadie, Double Liaison—Chimie des Peintures, No. 435-436, 1992, p. 28-34.

These photoinitiators include:

- α-hydroxyketones, such as 2-hydroxy-2-methyl-1-phenyl-1-propanone, sold for example under the names DAROCUR® 1173 and 4265, IRGACURE® 184, 2959, and 500 by the company BASF, and ADDITOL® CPK by CYTEC;
- α-aminoketones, in particular 2-benzyl-2-dimethylamino-1-(4-morpholinophenyl)-butanone-1, sold, for example, under the names Irgacure® 907 and 369 by the company BASF;
- aromatic ketones marketed, for example, under the name ESACURE® TZT by LAMBERTI; or the thioxanthones marketed, for example, under the name ESACURE® ITX by LAMBERTI, and quinones. These aromatic ketones most often require the presence of a hydrogen donor compound such as tertiary amines and especially alkanolamines. It is possible to mention the tertiary amine ESACURE® EDB sold by the company LAMBERTI.
- the α-dicarbonyl derivatives, the most common representative of which is benzyldimethylketal, marketed under the name IRGACURE® 651 by BASF. Other commercial products are marketed by LAMBERTI under the name ESACURE® KB1, and
- acylphosphine oxides, such as, for example, bis-acylphosphine oxides (BAPO) marketed for example under the names Irgacure® 819, 1700, and 1800, DAROCUR® 4265, LUCIRIN® TPO, and LUCIRIN® TPO-L by the company BASF.

Among photoinitiators, mention may also be made of aromatic ketones such as benzophenone, phenylglyoxylates, such as the methyl ester of phenylglyoxylic acid, oxime esters, such as [1-(4-phenylsulfanylbenzoyl) heptylideneamino] benzoate, sulphonium salts, iodonium salts and oxime sulphonates.

According to one embodiment, the composition C2 may further comprise an additional monomer or polymer capable of improving the properties of the microcapsule envelope and/or of giving new properties to the microcapsule envelope.

Among these additional monomers or polymers, may be mentioned monomers or polymers bearing a group sensitive to pH, temperature, UV or IR.

These additional monomers or polymers may induce the rupture of the solid microcapsules and subsequently the release of their contents after stimulation via pH, temperature, UV or IR.

These additional monomers or polymers may be chosen from monomers or polymers bearing at least one reactive functional group chosen from the group consisting of acrylate, methacrylate, vinyl ether, N-vinyl ether, mercaptoester, thiolene, siloxane, epoxy, oxetane and urethane isocyanate and peroxide functions, and also bearing one of the following groups:

- a hydrophobic group such as a fluorinated group, for example trifluoroethyl methacrylate, trifluoroethyl acrylate, tetrafluoropropyl methacrylate, pentafluoropropyl acrylate, hexafluorobutyl acrylate, or fluorophenyl isocyanate; a group sensitive to pH such as primary, secondary or tertiary amines, carboxylic acids, phosphate, sulfate, nitrate or carbonate groups;
- a UV-sensitive or UV-cleavable group (or photochromic group) such as azobenzene, spiropyran, 2-diazo-1,2-naphthoquinone, o-nitrobenzyl, thiol, or 6-nitro-veratroyloxycarbonyl, for example polyethylene oxide)-block-poly(2-nitrobenzylmethacrylate), and other block copolymers, as described in particular in Liu et al., Polymer Chemistry 2013, 4, 3431-3443;
- an IR-sensitive or IR-cleavable group such as o-nitrobenzyl or 2-diazo-1,2-naphthoquinone, for example the polymers described in Liu et al., Polymer Chemistry 2013, 4, 3431-3443; and
- a temperature-sensitive group such as poly(N-isopropylacrylamide).

Step b)

During step b), the emulsion (E1) obtained in step a) is added to a composition C3, this step being carried out with stirring, which means that the composition C3 is agitated, typically mechanically, while the emulsion (E1) is added in order to emulsify the mixture of compositions C1, C2 and C3.

The addition of the emulsion (E1) in the composition C3 is typically carried out dropwise.

During step b), the emulsion (E1) is at a temperature between 15° C. and 60° C. During step b), the composition C3 is at a temperature between 15° C. and 60° C.

Under the addition conditions of step b), the compositions C2 and C3 are not miscible with each other, which means that the amount (by weight) of the composition C2 capable of being solubilized in the composition C3 is less than or equal to 5%, preferably less than 1%, and preferably less than 0.5%, relative to the total weight of composition C3, and that the amount (by weight) of the composition C3 capable of being solubilized in composition C2 is less than or equal to 5%, preferably less than 1%, and preferably less than 0.5%, relative to the total weight of composition C2.

Thus, when the emulsion (E1) comes into contact with the composition C3 with stirring, the latter is dispersed in the form of drops, called double drops, the dispersion of these emulsion drops (E1) in the continuous phase C3 being called emulsion (E2).

Typically, a double drop formed during step b) corresponds to a single drop of composition C1 as described above, surrounded by a composition envelope C2 which completely encapsulates the single drop.

The double drop formed during step b) may also comprise at least two single drops of composition C1, the single drops being surrounded by a composition envelope C2 which completely encapsulates the single drops.

Thus, the double drops comprise a core consisting of one or more single drops of composition C1, and a layer of composition C2 surrounding the core.

The resulting emulsion (E2) is generally a double polydisperse emulsion (C1-in-C2-in-C3 emulsion or C1/C2/C3 emulsion), which means that the double drops do not have a clear size distribution in the emulsion (E2).

The immiscibility between the compositions C2 and C3 makes it possible to avoid mixing between the layer of composition C2 and the composition C3 and thus ensures the stability of the emulsion (E2).

The immiscibility between the compositions C2 and C3 also makes it possible to prevent the active ingredient of the composition C1 from migrating from the core of the drops to the composition C3.

To implement step b), it is possible to use any type of stirrer usually used to form emulsions, such as, for example, a mechanical stirrer, a static emulsifier, an ultrasonic homogenizer, a membrane homogenizer or a high pressure homogenizer, a colloid mill, a high shear disperser or a high speed homogenizer, may be used.

Composition C3

According to the invention, the viscosity of the composition C3 at 25° C. is higher than the viscosity of the emulsion (E1) at 25° C.

Preferably, the viscosity of the composition C3 at 25° C. is between 3,000 mPa·s and 100,000 mPa·s, preferably between 5,000 mPa·s and 80,000 mPa·s, for example between 7,000 mPa·s. and 70,000 mPa·s.

According to this embodiment, given the very high viscosity of the continuous phase formed by the composition C3, the destabilization rate of the double drops of the emulsion (E2) is significantly slow compared to the duration of the method of the invention, which then provides a kinetic stabilization of the emulsions (E2) and then (E3) until the polymerization of the capsule envelope is completed. Once the capsules are polymerized, they are thermodynamically stable.

Thus, the very high viscosity of the composition C3 ensures the stability of the emulsion (E2) obtained at the end of step b).

Preferably, the interfacial tension between compositions C2 and C3 is low. The low interfacial tension between the compositions C2 and C3 also advantageously makes it possible to ensure the stability of the emulsion (E2) obtained at the end of step b).

According to one embodiment, the ratio between the emulsion volume (E1) and the composition volume C3 varies between 1:10 and 10:1. Preferably, this ratio is between 1:9 and 3:1, preferably between 1:9 and 1:1.

This ratio may be adapted to control the total amount of encapsulated active ingredient among the resulting population of polymerized microcapsules.

According to one embodiment, the composition C3 comprises at least one branched polymer, preferably having a molecular weight greater than 5,000 $g \cdot mol^{-1}$, preferably between 10,000 g·mol$^{-1}$ and 500,000 g·mol$^{-1}$, for example between 50,000 g·mol$^{-1}$ and 300,000 g·mol$^{-1}$.

"Branched polymer" is understood to mean a polymer having at least one branch point between its two end groups, a branch point being a point of a chain on which is fixed a side chain also called a branch or hanging chain.

Among branched polymers may be mentioned, for example, graft or comb polymers, or star polymers or dendrimers.

According to one embodiment, the composition C3 comprises at least one polymer with a molecular weight of greater than 5,000 g·mol$^{-1}$, preferably between 10,000 g·mol$^{-1}$ and 500,000 g·mol$^{-1}$, for example between 50,000 g·mol$^{-1}$ and 300,000 g·mol$^{-1}$.

As a polymer that may be used in the composition C3, mention may be made of the following compounds, used alone or mixed together:

- cellulose derivatives, such as cellulose ethers: methyl cellulose, ethyl cellulose, hydroxyethyl cellulose, methylhydroxyethyl cellulose, ethylhydroxyethyl cellulose, carboxymethyl cellulose, hydroxypropyl cellulose or methylhydroxypropyl cellulose;
- polyacrylates (also called carbomers), such as polyacrylic acid (PAA), polymethacrylic acid (PMAA), poly(hydroxyethyl methacrylate) (pHEMA), poly(N-2-hydroxypropyl methacrylate) (pHPMA);
- polyacrylamides such as poly(N-isopropylacrylamide) (PNIPAM);
- polyvinylpyrrolidone (PVP) and its derivatives;
- polyvinyl alcohol (PVA) and its derivatives;
- poly(ethylene glycol), poly(propylene glycol) and their derivatives, such as poly(ethylene glycol) acrylate/methacrylate, poly(ethylene glycol) diacrylate/dimethacrylate, polypropylene carbonate;
- polysaccharides such as carrageenans, carob gum or tara gums, dextran, xanthan gums, chitosan, agarose, hyaluronic acids, gellan gum, guar gum, gum arabic, gum tragacanth, gum diutane, oat gum, karaya gum, ghatti gum, curdlan gum, pectin, konjac gum, starch;
- protein derivatives such as gelatin, collagen, fibrin, polylysine, albumin, casein;
- silicone derivatives such as polydimethylsiloxane (also called dimethicone), alkyl silicones, aryl silicones, alkyl aryl silicones, polyethylene glycol dimethicones, polypropylene glycol dimethicone;
- waxes, such as diester waxes (alkanediol diesters, hydroxyl acid diesters), triester waxes (triacylglycerols, triesters of alkane-1,2-diol, ω-hydroxy acid and fatty acid, esters of hydroxymalonic acid, fatty acid and alcohol, triesters of hydroxyl acids, fatty acid and fatty alcohol, triesters of fatty acid, hydroxyl acid and diol) and polyester waxes (polyesters of fatty acids). The fatty acid esters which may be used as waxes in the context of the invention are, for example, cetyl palmitate, cetyl octanoate, cetyl laurate, cetyl lactate, cetyl isononanoate and stearate. cetyl, stearyl stearate, myristyl stearate, cetyl myristate, isocetyl stearate, glyceryl trimyristate, glyceryl tripalmitate, glyceryl monostearate, or cetyl glyceryl palmitate;
- fatty acids that may be used as waxes such as cerotic acid, palmitic acid, stearic acid, dihydroxystearic acid, behenic acid, lignoceric acid, arachidic acid, myristic acid, lauric acid, tridecyclic acid, pentadecyclic acid, margaric acid, nonadecyclic acid, henicosylic acid, tricosylic acid, pentacosylic acid, heptacosylic acid, montanic acid or nonacosylic acid;
- fatty acid salts, in particular fatty acid aluminum salts, such as aluminum stearate, hydroxyl aluminum bis(2-ethylhexanoate);
- isomeric jojoba oil;
- hydrogenated sunflower oil;
- hydrogenated coconut oil;
- hydrogenated lanolin oil;
- castor oil and its derivatives, especially modified hydrogenated castor oil or compounds obtained by esterification of castor oil with fatty alcohols;
- polyurethanes and their derivatives;
- styrenic polymers such as styrene butadiene; polyolefins such as polyisobutene.

According to one embodiment, the composition C3 comprises solid particles such as clays, silicas and silicates.

As solid particles that may be used in the composition C3, mention may be made of clays and silicates belonging in particular to the category of phyllosilicates (also known as layered silicas). By way of example of a silicate that may be used in the context of the invention, mention may be made of bentonite, hectorite, attapulgite, sepiolite, montmorillonite, saponite, sauconite, nontronite, kaolinite, talc, sepiolite, chalk. Fumed synthetic silicas may also be used. The clays, silicates and silicas mentioned above may advantageously be modified by organic molecules such as polyethers, ethoxylated amides, quaternary ammonium salts, long-chain diamines, long-chain esters, polyethylene glycols, polypropylene glycols.

These particles may be used alone or mixed together.

According to one embodiment, the composition C3 comprises at least one polymer with a molecular weight greater than 5,000 g·mol$^{-1}$ and solid particles. Any mixture of the compounds mentioned above may be used.

Step c)

In step c), the emulsion (E2), consisting of polydispersed drops dispersed in a continuous phase, is subjected to shear, for example in a mixer, at a low shear rate, i.e. less than 1,000 s$^{-1}$.

According to one embodiment, the shear rate applied in step c) is between 10 s$^{-1}$ and 1000 s$^{-1}$.

Preferably, the shear rate applied in step c) is strictly less than 1000 s$^{-1}$.

During step c), the emulsion (E2) is introduced into a mixer and is then subjected to shearing which results in the formation of a third emulsion, the emulsion (E3). This emulsion (E3) is chemically identical to the emulsion (E2) but it consists of monodisperse double drops, and non-polydisperse as (E2).

Typically, the emulsion (E3) consists of a dispersion of double drops comprising a core consisting of one or more single drops of composition C1, and a layer of composition C2 surrounding the core, the double drops being dispersed in composition C3.

The difference between the emulsion (E2) and the emulsion (E3) is the variation in size of the double drops: the drops of the emulsion (E2) are polydisperse in size, whereas the drops of the emulsion (E3) are monodisperse thanks to the fragmentation mechanism taking place during step c).

Emulsion drops (E2) can only be fragmented effectively into fine, monodisperse emulsion drops (E3) if high shear stress is applied thereto.

The shear stress a applied to a drop of emulsion (E2) is defined as the tangential force per unit area of drop resulting from the macroscopic shear applied to the emulsion during its stirring during step c).

The shear stress σ (expressed in Pa), the viscosity of the composition C3 η (expressed in Pa·s), and the shear rate γ

(expressed in $s^{-1}$) applied to the emulsion (E2) during its stirring at course of step c) are related by the following equation:

$$\sigma=\eta\gamma$$

Thus, the high viscosity of the composition C3 makes it possible to apply a very high shear stress to the emulsion drops (E2) in the mixer, even if the shear rate is low and the shear inhomogeneous.

To implement step c), it is possible to use any type of stirrer usually used to form emulsions, such as, for example, a mechanical stirrer, a static emulsifier, an ultrasonic homogenizer, a membrane homogenizer or a high pressure homogenizer, a colloid mill, a high shear disperser or a high speed homogenizer, may be used.

According to a preferred embodiment, a simple emulsifier such as a mechanical stirrer with a vane or a static emulsifier is used to implement step a). In fact, this is possible because the method of the invention requires neither controlled shear nor shear greater than 1000 $s^{-1}$.

Step d)

Step d) consists of subjecting the emulsion (E3) to photopolymerization, which will allow the photopolymerization of the composition C2.

This step will make it possible to obtain microcapsules encapsulating the active ingredient as defined above.

According to one embodiment, step d) consists in exposing the emulsion (E3) to a light source capable of initiating the photopolymerization of the composition C2.

Preferably, the light source is a source of UV light.

According to one embodiment, the UV light source emits in the wavelength range of between 100 nm and 400 nm.

According to one embodiment, the emulsion (E3) is exposed to a light source for less than 15 minutes, and preferably for 5 to 10 minutes.

During step d), the envelope of the aforementioned double drops, consisting of photocurable composition C2, is crosslinked and thus converted into a viscoelastic polymeric envelope, encapsulating and protecting the active ingredient from its release in the absence of a mechanical trigger.

The composition obtained at the end of step d), comprising solid microcapsules dispersed in the composition C3, is ready for use and may be used without any additional step of post-treatment of the capsules being required.

The thickness of the envelope of the microcapsules thus obtained is typically between 10 nm and 2.5 μm, preferably between 100 nm and 1000 nm.

According to one embodiment, the solid microcapsules obtained at the end of step d) are devoid of water and/or surfactant.

The method of the invention has the advantage of not requiring water in any of the steps described. The method of the invention thus makes it possible to encapsulate compounds that are sensitive to water.

The method of the invention has the advantage of not requiring a surfactant, in any of the steps described. The method of the invention thus makes it possible to reduce the presence of additives which could modify the properties of the final product obtained after release of the active ingredient.

EXAMPLES

Example 1: Preparation of Solid Microcapsules Thanks to a Highly Viscous C3 Phase and Low Shear This example demonstrates the use of a viscous C3 composition making it possible to obtain monodisperse capsules of size less than 20 μm even by applying a very low shear to the double emulsion (E2).

Composition of C1, C2 and C3:

The composition C1 is a solution of alginate (active ingredient) at 5% by weight.

The composition C2 is a mixture of 69% by weight of CN981 polymer (polyacrylate oligomer of the Sartomer brand, Arkema); 30% by weight of hexanediol diacrylate (crosslinking agent), and 1% by weight of Darocure 1173 (photoinitiator).

The composition C3 is a solution of alginate at 15% by weight, viscosity 63,000 $s^{-1}$ at 25° C.

Manufacture of Microcapsules:

A mechanical stirrer (Heidolph RZR 2021) equipped with a 3 cm diameter deflocculating stirring propeller is used to carry out all the emulsification steps.

Step a): the composition C1 is added dropwise to the composition C2 at a ratio C1:C2=30:70 by weight with stirring at 500 rpm.

Step b): the emulsion (E1) obtained in the preceding step is added dropwise to the composition C3 at a ratio E1:C3=10:90 by weight with stirring at 500 rpm.

Step c): The emulsion (E2) thus obtained is stirred at 500 rpm for 10 minutes. The shear applied by a stirring propeller is very poorly controlled. Under the conditions of step c), the shear applied to the emulsion (E2) may be estimated to be less than 500 $s^{-1}$ (for the details of the calculation, refer to: Metzner A B, Otto R E. Agitation of non-Newtonian fluids AIChE J (1957) 3: 3-10, Wu, J et al., Estimation of agitator flow shear rate AIChE J (2006) 52: 2323-2332).

Step d): the monodisperse emulsion (E3) thus obtained is irradiated for 10 minutes using a UV light source (Dymax LightBox ECE 2000) having a maximum light intensity of 0.1 $W/cm^2$ at a 365 nm wavelength, to allow cross-linking of the capsules.

The size distribution of the capsules thus obtained is measured by light scattering technique using a Mastersizer 3000 (Malvern Instruments) equipped with a Hydro SV cell. The average size of the capsules is measured at 26 μm. The width at half height of the size distribution (considered as a simple way of evaluating the monodispersity of the capsules) is measured at 31 μm.

Example 2: Preparation of Solid Microcapsules Thanks to a Highly Viscous C3 Phase and High Shear This example demonstrates that with the same formulation as in Example 1, the application of high shear does not improve the monodispersity of the capsules obtained.

In this example, an emulsion (E2) that is identical in all respects to that of Example 1, is first obtained. This is then separated into 2 equal volume fractions which are introduced into a high shear type Couette cell manufactured by the company TSR33. This cell consists of two concentric cylinders, one mobile and the other fixed, separated by a gap of 100 μm. The rotation of the movable cylinder makes it possible to apply a uniform shear to all the emulsion contained in the gap. The first fraction of the emulsion (E2) is subjected to a shear of 6,300 $s^{-1}$ and the second fraction to a shear of 14,300 $s^{-1}$.

The emulsions (E3) thus obtained are irradiated for 10 minutes using a UV light source (Dymax LightBox ECE 2000) having a maximum light intensity of 0.1 $W/cm^2$ at a wavelength of 365 nm. to allow the crosslinking of the capsules.

The capsule size distribution thus obtained is measured by light scattering technique using a Mastersizer 3000 (Malvern Instruments) equipped with a Hydro SV cell. The average size of the capsules and the width at mid-height of the size distribution obtained are summarized in the table below and compared with the values obtained in Example 1. It is clear that the application of a high shear does not decrease the average size and the monodispersity of the capsules.

| | | Example 2 | |
|---|---|---|---|
| Shear | Example 1 <500 $s^{-1}$ (deflocculating vane) | 6 300 $s^{-1}$ (Couette cell) | 14 300 $s^{-1}$ (Couette cell) |
| Average size | 5.0 μm | 5.2 μm | 5.8 μm |
| Width at mid-height of the distribution | 5.5 μm | 5.8 μm | 6.8 μm |

Example 3: Preparation of Solid Microcapsules Thanks to a Low-Viscosity C3 Phase and Different Shear Values This example demonstrates that when a composition C3 with a viscosity of less than 2000 mPa·s at 25° C. is used to make microcapsules, it is necessary to resort to an additional step of high shear to obtain monodisperse size microcapsules. less than 20 μm.

Composition of C1, C2 and C3:

The composition of C1 and C2 is identical to that of Example 1.

The composition C3 is a solution of alginate at 5% by mass, viscosity 1500 mPa·s.

Manufacture of Microcapsules:

Steps a) and b) are performed identically to those of Example 1.

Step c): The emulsion (E2) obtained is separated into 3 fractions numbered 1, 2, and 3 of equal volume which are subjected to the following shear conditions:

| | Shear conditions |
|---|---|
| Fraction 1 | Pale deflocculating, shear <500 $s^{-1}$ |
| Fraction 2 | Couette cell, shear 6 300 $s^{-1}$ |
| Fraction 3 | Couette cell, shear 14 300 $s^{-1}$ |

Step d): Fractions 1, 2, and 3 are irradiated for 10 minutes using a UV light source (Dymax LightBox ECE 2000) having a maximum light intensity of 0.1 W/$cm^2$ at a 365 nm wavelength, to allow crosslinking of the capsules.

The size distribution of the capsules thus obtained is measured by light scattering technique using a Mastersizer 3000 (Malvern Instruments) equipped with a Hydro SV cell. The average size of the capsules and the width at mid-height of the size distribution obtained are summarized in the table below. It is clear that it is necessary to apply a shear of at least 6,300 $s^{-1}$ to obtain monodisperse capsules less than 20 μm in size.

| | Average size | Width at mid-height of the distribution |
|---|---|---|
| Fraction 1 | 26 μm | 31 μm |
| Fraction 2 | 16 μm | 15 μm |
| Fraction 3 | 12.5 μm | 12 μm |

What is claimed is:

1. A method for preparing solid microcapsules comprising the steps of:

a) adding, with stirring, a composition C1, comprising at least one active ingredient, in a photocrosslinkable polymer composition C2, the compositions C1 and C2 not being miscible with each other, wherein an emulsion (E1) comprising drops of the composition C1 dispersed in the composition C2, is obtained;

b) adding, with stirring, the emulsion (E1) in a composition C3, the compositions C2 and C3 not being miscible with each other, the viscosity of the composition C3 being greater than the viscosity of the emulsion (E1), and being greater than 2,000 mPa·s at 25° C., wherein a double emulsion (E2) comprising drops dispersed in the composition C3, is obtained;

c) applying shear to the emulsion (E2), the applied shear rate being less than 1000 $s^{-1}$, wherein a double emulsion (E3) is obtained comprising controlled-size drops dispersed in the composition C3; and d) polymerizing by photopolymerization the composition C2, wherein solid microcapsules dispersed in the composition C3 are obtained.

2. The method according to claim 1, wherein the composition C2 is a liquid the viscosity of which at 25° C. is between 500 mPa·s and 100 000 mPa·s.

3. The method according to claim 1, wherein the composition C2 comprises at least one monomer or polymer, at least one crosslinking agent, and at least one photoinitiator.

4. The method according to claim 3, wherein the composition C2 comprises from 0.001% to 70% by weight of crosslinking agent relative to the total weight of the composition C2.

5. The method according to claim 1, wherein the active ingredient is solubilized in the composition C1, or is dispersed in the form of solid particles in the composition C1.

6. The method according to claim 1, wherein the composition C3 comprises at least one branched polymer, and/or at least one polymer of molecular weight greater than 5,000 g·$mol^{-1}$, and/or solid particles.

7. The method according to claim 1, wherein the viscosity of composition C3 at 25° C. is between 1000 mPa·s and 100,000 mPa·s.

8. The method according to claim 1, wherein the shear rate applied in step c) is between 10 $s^{-1}$ and 1000 $s^{-1}$.

9. The method according claim 1, wherein step d) comprises exposing the emulsion (E3) to a light source capable of initiating the photopolymerization of the composition C2.

10. The method according to claim 9, wherein the light source is a UV light source.

11. The method according to claim 6, wherein the composition C3 comprises at least one branched polymer with a molecular weight greater than 5000 g·$mol^{-}$.

12. The method according to claim 6, wherein the solid particles are silicates.

* * * * *